United States Patent [19]

Featherstone et al.

[11] Patent Number: 4,874,315

[45] Date of Patent: Oct. 17, 1989

[54] METHOD FOR BONDING OF RESTORATIVE MATERIALS TO A TOOTH

[75] Inventors: John D. B. Featherstone; Lyndon F. Cooper, both of Rochester; Michael L. Myers, Pittsford, all of N.Y.; Dennis G. A. Nelson, Wellington, New Zealand

[73] Assignee: Eastman Dental Center, Rochester, N.Y.

[21] Appl. No.: 16,250

[22] Filed: Feb. 19, 1987

[51] Int. Cl.$^4$ ................................................ A61C 5/00
[52] U.S. Cl. ....................................... 433/215; 106/35; 433/226; 433/228.1
[58] Field of Search ............... 106/35; 427/2; 433/215, 433/217, 226, 228.1

[56] References Cited

U.S. PATENT DOCUMENTS

| | | | |
|---|---|---|---|
| 4,222,128 | 9/1980 | Tomonaga et al. | 106/35 |
| 4,224,072 | 9/1980 | Stewart | 106/35 |
| 4,375,961 | 3/1983 | Brooks | 433/159 |
| 4,443,197 | 4/1984 | Fusayama et al. | 106/35 |
| 4,492,577 | 1/1985 | Farris al. | 433/201.1 |
| 4,521,194 | 6/1985 | Myers et al. | 433/215 |

OTHER PUBLICATIONS

Stern, R., "Dentistry and The Laser", in *Laser Applications in Medicine and Biology*, vol. 2, ed. M. L. Wolbarsht (1974).

Featherstone, J. et al, *Advances in Dental Research*, 1(1):21-26, Oct. 1987.

Cooper et al, *Journal of Prosthetic Dentistry*, vol. 60, No. 1, pp. 45-49, Jul. 1988.

Nelson et al, *Canes Research*, vol. 21, pp. 411-426, 1987.

Primary Examiner—Paul Lieberman
Assistant Examiner—Linda D. Skaling
Attorney, Agent, or Firm—Martin Lukacher

[57] ABSTRACT

A method for bonding of restorative materials, such as composite resins, to the surface of a tooth wherein the surface of the tooth is pretreated with a carbon dioxide laser of low energy density without damaging surrounding tissues or the underlying pulp of the tooth.

14 Claims, 1 Drawing Sheet

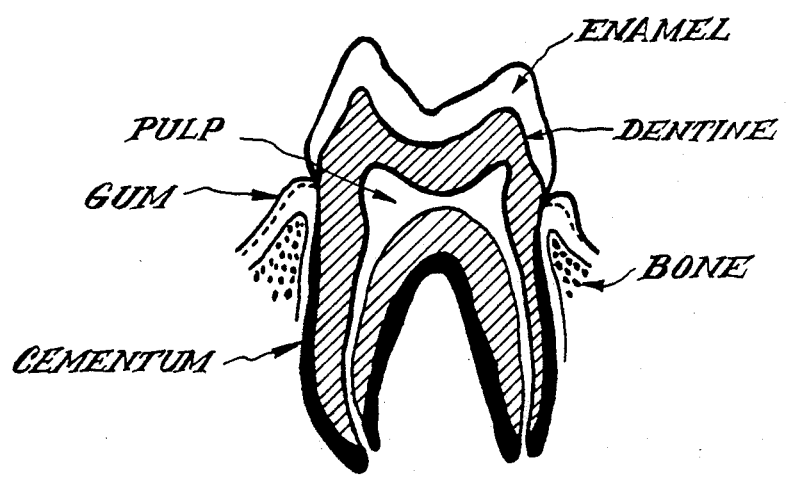

METHOD FOR BONDING OF RESTORATIVE MATERIALS TO A TOOTH

DISCLOSURE

The present invention relates to a method for treating the surface of a tooth to improve the bonding of restorative materials. More specifically, the invention relates to a method of treating the surface of a tooth with a low energy carbon dioxide laser at a wavelength of between 9.0 and 11.0 μm, and then applying a restorative material to the treated surface. This method results in a significant increase in bond strength compared to pretreatment methods currently being practiced.

The use of lasers in dentistry has been considered since their advent. Lasers have been considered for use in cutting/drilling of dental enamel. To be effective, high energy-density pulses (i.e., approximately $10^4$ J per $cm^2$) were used. The long interaction times required coupled with the high energy-density created the potential for serious damage to underlying pulp and the surrounding soft oral tissue.

Subsequently, low energy-density pulses were considered and were investigated for use in the treatment of enamel for the prevention of dental caries formation. Such low energy-densities avoided the potential for damage but caused the fusion of enamel crystallites at the enamel surface. This resulted from the relatively long interaction times used (i.e., 50 ms to 2s).

Prevention of dental caries is one of the principal aims of modern dentistry. Beyond prevention, there exists an extensive area of dentistry, namely the repair/-reconstruction of the tooth. This involves the application of a restorative material to the surface of a tooth. Such restorative materials include composite resins, such as Bis-GMA based and urethane based polymers and other materials such as ceramics, alloys, ionomer cements and polymers. Although cosmetic appearance is important when restorative materials are used, more important is the degree to which the restorative material bonds to the tooth surface. Poor bond strength can result in discoloration of the tooth, recurrent decay, loss of tooth substance, significant discomfort and potential embarrassment to the patient. Thus, a high bond strength is desired.

In preparing a tooth for the application of a restorative material, two methods previously have been used. First, traditional retentive pins and undercuts have been used to aid mechanical retention of restorations. More recently, acid etching has been used to roughen the tooth surface to allow retention of polymeric materials. Alternatively, chemicals, such as glass ionomer cements and dentin bonding agents, can be used to achieve a similar result. While both methods are useful particularly for dental enamel, they are inefficient for dentin.

It is an object of the present invention to significantly increase the bonding strength of a restorative material to a tooth when compared with prior known mechanical and chemical methodologies. When the present method is used in connection with bonding a composite resin to dentin, bonding strengths can be improved by 300 percent.

A feature of this invention is that surface areas of a tooth to be treated can be easily limited, avoiding damage to pulp or the surrounding oral tissue.

BRIEF DESCRIPTION OF THE DRAWINGS

Other objects, features and advantages of this invention, as well as the best mode for practice thereof, will become more apparent from a reading of the following detailed description of the invention which makes reference to the following drawing:

FIG. 1 is a cross-sectional, elevational view of a tooth.

Referring to FIG. 1, a tooth has essentially three layers. The outermost layer is comprised of enamel. Enamel is the hardest part of the tooth and forms a protective layer over the supporting body portion of the tooth. Enamel and dentin are mainly comprised of a mineral calcium phosphate (or apatite) surrounded by a matrix of protein and lipid.

Dentin comprises the principal mass of the tooth. In comparison with enamel, dentin has a higher organic (protein) content.

Beneath the dentin is the pulp. Pulp contains vessels and nerves and, therefore, is extremely sensitive to pressure and temperature. The intact enamel and dentin protect the pulp.

When a tooth becomes damaged by either physical or natural degenerative processes, the enamel may be eroded and/or the dentin exposed. This necessitates restoration. A restorative material may be used to cover the exposed surface. Restorative materials may comprise ceramics, alloys, glass ionomers, composite resins or polymers. They serve to protect the surface of the tooth from further damage.

To prepare a surface of a tooth for application of a restorative material, the surface (either enamel, cementum or dentin) should be treated to improve bonding. In an example of the present invention, treatment occurs by applying a low energy carbon dioxide laser to the exposed surface.

Dental mineral absorbs very little light in the visible region, but absorbs a large amount of light in the infrared region from 9 to 11 μm. Dental enamel, cementum and dentin contain the mineral carbonated apatite which has absorption bands in the infrared region due to phosphate, carbonate and hydroxyl groups in the crystal structure. As noted above, carbon dioxide gas lasers produce an infrared beam in this region.

A low energy density, short duration beam is used as a means of effecient energy transfer to the localised area of the tooth surface. In other words a pulsed low energy density beam obtained as by pulsed operation of a carbon dioxide laser and directed upon the area to be treated is used. This means that fusion, melting and recrystallization of the enamel cementin or dentin crystals exposed is confined to a thin (i.e., approximately 5 μm) surface region.

The beam may be in the form of a continuous wave or may be pulsed, as noted above. The effects achieved by pulsing the carbon dioxide laser are related to the energy levels chosen. Low energy levels of approximately 5 J avoid damage to surrounding oral tissue and pulp. By pulsing, however, peak power-density can be kept relatively constant (i.e., between $10^7$ and $10^8$ W per $cm^2$). Pulse energy-densities between 10 and 50 J per $cm^2$ are preferred. Optimum surface roughening has been found to occur at 50 J per $cm^2$. Pulses of 100–200 ns duration have been found to be optimum.

The transfer of light energy to heat at the tooth surface has been found be be efficient at wavelengths between 9.32 and 10.59 μm. Mineral structure is altered as well as surface morphology providing a chemically and physically attractive surface for improved bonding.

Thus, in the preferred embodiment, a carbon dioxide laser is pulsed, with pulses of 100–200 ns, at a wavelength of 9.32 $\mu$m, with a peak energy density of 50 J per cm$^2$. After this treatment step, a restorative material (preferably resin) can then be applied to achieve maximum bonding. The following example provides additional details and is illustrative of the best mode currently known for practicing the invention.

Thirty intact, non-carious human molar teeth were collected and washed in detergent, debrided of all soft tissue and cleaned ultrasonically in double deionized water (DDW) for five minutes. The teeth were divided into three groups. Twenty teeth were obliquely sectioned from buccal cusp tip to a point 1–2 mm apical to the cemento-enamel junction exposing a planed dentinal surface exhibiting a minimum diameter of 1 cm. Ten other molars were obliquely abraded on the buccal enamel surface with 600 grit paper to create a flat, polished enamel surface of no less than 0.6 cm in diameter. Of the 20 sectioned molar teeth (dentin specimens), 10 were immediately stored in DDW. The other 10 were mounted individually in modeling plastic and the cut dentin surface was laser irradiated.

A Lumonics TEA 103-1 tunable $CO_2$ gas laser was used to supply pulsed 9.32 $\mu$m wavelength (1073 cm$^{-1}$ wavenumber) radiation to the dentin surfaces. Thirty pulses, each 100–200 ns in duration and delivered at 0.67 Hz (i.e., over a period of 40 s) produced 30 individual 10–50 J per cm$^2$ energy doses.

The 10 lased dentin sections and 10 unlased dentin sections were washed for 30 seconds in 2% sodium hypochlorite and rinsed for 30 seconds in DDW. Following thorough drying with filtered compressed air, each dentin sample was coated with "Scotchbond" (3M Co., St. Paul, Minn.) and the excess was removed with compressed air. A second coat of "Scotchbond" was immediately applied and again the excess was removed by compressed air. "P-10" composite resin (a microfill Bis-GMA resin, 3M Co., St. Paul, Minn.) was mixed according to the manufacturer's recommendation, placed into 0.45 mm diameter gelatin capsules and polymerized to the bonded lased and unlased dentin surfaces. Excess composite resin was removed before the composite resin was set. Each bonded sample was placed in DDW. Enamel sections were etched with 37% phosphoric acid and "Scotchbond" was applied, according to the manufacturer's recommendations. Composite resin cylinders were bonded to the surface of the enamel.

All 30 samples were stored 24 hours at 25° C. in DDW. Mounting of samples into improved die stone bases for shear stress testing was achieved to insure that long axes of the cylinders were parallel to the platform of an Instron testing machine (Instron Corp., Canton, Mass.) and the prepared surface of the enamel or dentin was parallel to the vertical stylus. The samples were tested for shear strength of the bonded composite to the three different prepared molar surfaces by using the Istron testing machine. Shear stress was applied to the composite cylinder/tooth interface with a machined stylus. All samples were measured using a 5.0 Kg load delivered at a 0.01 cm/min cross head speed. Shear strengths at the point of bond failure were measured.

The laser irradiation produced significant chemical and morphological changes in the dentin surface as compared to normal dentin. Localizing melting and recrystallization of the surface dentin produced fungiform projections covered with a glaze-like surface.

Comparison of mean shear strengths of the lased dentin sections to unlased dentin sections indicated a 300% increase in bond strength of a self curing composite resin via "Scotchbond" dentin adhesive to the dentin surface. The measurements of 26.68 kg/cm$^2$ ($\pm$13.61) for unlased dentin and 77.22 kg/cm$^2$ ($\pm$14.02) for lased dentin (p<0.005) were significant. Thus, laser irradiation of dentin significantly increases composite resin-dentin bond strengths.

The laser irradiation of the surface area produced chemical charges and a surface morphology which enhances the mechanical and chemical bond of composite resin. The restorative material adapts to the undercuts and spaces between the dentinal projections in a manner similar to acid-etching techniques on enamel and electro-chemical etching of metals.

Variations and modifications of the herein described method, within the scope of the invention, may suggest themselves to those skilled in the art. Accordingly, the foregoing descriptions should be taken in an illustrative and not in a limiting sense.

We claim:

1. A method for treating a tooth with a restorative material comprising the steps of pretreating at least a portion of the surface area of the dentin or cementum of said tooth with light from a laser, which is of a wavelength between 9.0 and 11.0 micrometers for a duration sufficient to apply about 5 J of laser energy to said dentin or cementum, and then applying a restoring material to the pretreated surface area of said tooth.

2. The method as set forth in claim 1 wherein the surface area is dentin.

3. The method as set forth in claim 1 wherein the surface is cementum.

4. The method as set forth in claim 1 wherein said laser is pulsed to produce pulses of light of sufficiently short duration and for a sufficiently long period of time to provide said laser energy of about 5 J.

5. The method as set forth in claim 4 wherein the duration of each pulse is between 100–200 ns.

6. The method as set forth in claim 1 wherein said laser energy is applied in pulses of light, the peak energy density of which is sufficiently low to avoid irreversible damage to the tooth's surrounding oral tissue or to pulp.

7. The method as set forth in claim 1 wherein the wavelength is between 9.32 and 10.59 $\mu$m.

8. The method as set forth in claim 4 wherein the pulse energy-density is between 10–50 J per cm$^2$.

9. The method according to claim 1 wherein said step of applying a restorative material comprises applying a plurality of layers of said material to said surface sufficient to form a bond.

10. The method according to claim 9 wherein said restorative material (comprises) is selected from the group consisting of polymers, ionomer cements, alloys, ceramics and composite resins.

11. The method according to claim 9 wherein said composite resin is a microfill Bis-GMA resin.

12. A method for treating a tooth with a restorative material comprising the steps of pretreating dentin or cementum with a level of laser energy which is sufficiently low so that fusion, melting and recrystalization of the dentin or cementum is confined to a thin, approximately 5 micrometer thick region extending into the dentin or cementum below the surface thereof said laser energy having a wavelength between 9.0 and 11.0 micrometers, and then applying a restorative material to the pretreated dentin or cementum.

13. The method according to claim 1 wherein said laser is a carbon dioxide laser.

14. The method according to claim 12 wherein said laser is a carbon dioxide laser.

* * * * *